US011699512B2

(12) United States Patent
Noh

(10) Patent No.: US 11,699,512 B2
(45) Date of Patent: Jul. 11, 2023

(54) METHOD AND SYSTEM FOR CONSTRUCTING TRAINING PROGRAM FOR IMPROVING SYMPTOMS OF MILD COGNITIVE IMPAIRMENT PATIENT

(71) Applicant: EMOCOG Co., Ltd., Seoul (KR)

(72) Inventor: Yoo Hun Noh, Yangju-si (KR)

(73) Assignee: EMOCOG CO., LTD., Seoul (KR)

( * ) Notice: Subject to any disclaimer, the term of this patent is extended or adjusted under 35 U.S.C. 154(b) by 0 days.

(21) Appl. No.: 17/569,288

(22) Filed: Jan. 5, 2022

(65) Prior Publication Data

US 2023/0047533 A1  Feb. 16, 2023

(30) Foreign Application Priority Data

Aug. 9, 2021 (KR) .......................... 10-2021-0104738
Nov. 10, 2021 (KR) .......................... 10-2021-0153942

(51) Int. Cl.
*G09B 7/00* (2006.01)
*G16H 20/70* (2018.01)
(Continued)

(52) U.S. Cl.
CPC .......... *G16H 20/70* (2018.01); *G09B 19/0053* (2013.01); *G09B 19/02* (2013.01)

(58) Field of Classification Search
CPC . G09B 5/02; G09B 19/00; G09B 7/04; G16H 20/70; A61B 5/16
See application file for complete search history.

(56) References Cited

U.S. PATENT DOCUMENTS 6,022,221 A * 2/2000 Boon ....................... G09B 7/04
                                                                434/323
6,306,086 B1 * 10/2001 Buschke ................. G16H 50/30
                                                                273/273
(Continued)

FOREIGN PATENT DOCUMENTS

KR    10-2013-0087075 A    8/2013
KR    10-2019-0043107 A    4/2019
(Continued)

OTHER PUBLICATIONS

Office Action dated Dec. 29, 2021 in Korean Application No. 10-2021-0153942.
(Continued)

*Primary Examiner* — Peter R Egloff
(74) *Attorney, Agent, or Firm* — Knobbe, Martens, Olson & Bear, LLP

(57) ABSTRACT

This application relates to a method of constructing a training program for improving symptoms of a mild cognitive impairment patient. In one aspect, the method includes arranging, on designated days, direct training algorithms regarding at least one of visualization, fusion, or semantic word fluency directly related to a cognitive function area and controlling the arranged direct training algorithms to be output to a user terminal according to the designated days, and receiving a result value from the user terminal. The method may also include calculating an achievement level for each direct training algorithm, based on the result value, and determining one of the direct training algorithms based on the calculated achievement level. The method may further include rearranging the direct training algorithms, together with the determined direct training algorithm based on both the calculated achievement level and a training (Continued)

algorithm matched to the determined direct training algorithm.

16 Claims, 5 Drawing Sheets

(51) Int. Cl.
　　*G09B 19/00*　　　(2006.01)
　　*G09B 19/02*　　　(2006.01)

(56) References Cited

U.S. PATENT DOCUMENTS

| | | | | |
|---|---|---|---|---|
| 6,652,283 | B1* | 11/2003 | Van Schaack | G09B 7/04 434/323 |
| 7,186,116 | B2* | 3/2007 | Klingberg | G09B 7/04 434/362 |
| 7,357,640 | B2* | 4/2008 | Berman | G09B 19/00 434/323 |
| 2007/0299319 | A1* | 12/2007 | Chan | A61B 5/16 600/300 |
| 2017/0046971 | A1 | 2/2017 | Moreno | |
| 2018/0055433 | A1* | 3/2018 | Ally | A61B 3/02 |

FOREIGN PATENT DOCUMENTS

| | | |
|---|---|---|
| KR | 10-2020-0066578 A | 6/2020 |
| KR | 10-2166022 B1 | 10/2020 |
| KR | 10-2021-0062456 A | 5/2021 |
| KR | 10-2306863 B1 | 9/2021 |
| KR | 10-2308317 B1 | 9/2021 |
| KR | 10-2307414 B1 | 10/2021 |
| KR | 10-2307836 B1 | 10/2021 |

OTHER PUBLICATIONS

Notice of Allowance dated Mar. 31, 2022 in Korean Application No. 10-2021-0153942.

Kim et al., "Standardization and Validation of Big Five Inventory—Korean Version(BFI-K) in Elders", Biopsychiatry, vol. 17, No. 1, Feb. 2010.

Chang et al., "Reliability and Validity of the Korean Version of Memory Impairment Screen (MIS-K) as a Dementia Screening Instrument", J Korean Assoc Soc Psychiatry vol. 13, No. 1, 2008, pp. 3-9.

Kang et al., "A normative study of the Korean version of Controlled Oral Word Association Test (COWAT) in the elderly", Korean Journal of Clinical Psychology, 2000, vol. 19, No. 2, 385-392.

Kang et al., "A Normative Study of the Digit Span Test for the Elderly", Korean Journal of Clinical Psychology 21(4), Nov. 2002, 911-922 (12 pages).

Kim et al., "Efficacy of Smart Speaker-Based Metamemory Training in Older Adults: Case-Control Cohort Study", J Med Internet Res 2021, vol. 23, iss. 2, e20177, http://www.jmir.org/2021/2/e20177/.

Kim et al., "Use of the PHQ-2/PHQ-9 Serial Screening Instrument for Detecting Major Depressive Disorder in Primary Care", Stress, vol. 19, No. 4, 2011, pp. 405-410.

Oyama et al., "Novel Method for Rapid Assessment of Cognitive Impairment Using High-Performance Eye-Tracking Technology", Scientific Reports (2019) 9:12932 https://doi.org/10.1038/s41598-019-49275-x.

Park et al., "Neural predictors of cognitive improvement by multi-strategic memory training based on metamemory in older adults with subjective memory complaints", Scientific Reports (2018) 8:1095 DOI:10.1038/s41598-018-19390-2.

Van Ede et al., "The Metamemory, Memory Strategy and Study Technique Inventory (MMSSTI): a factor analytic study", S. Afr. J. Psychol. 1996, 26(2).

Youn et al., "Brain structural changes after multi-strategic metamemory training in older adults with subjective memory complaints: A randomized controlled trial", Brain and Behavior. 2019;e01278. https://doi.org/10.1002/brb3.1278.

Youn et al., "Cognitive Improvement in Older Adults with Mild Cognitive Impairment: Evidence from a Multi-Strategic Metamemory Training", J. Clin. Med. 2020, 9, 362; doi:10.3390/jcm9020362.

Youn et al., "Multistrategic Memory Training with the Metamemory Concept in Healthy Older Adults", Psychiatry Investig 2011;8:354-361.

Extended European Search Report in EP Application No. 22150533.2 dated Jun. 7, 2022.

\* cited by examiner

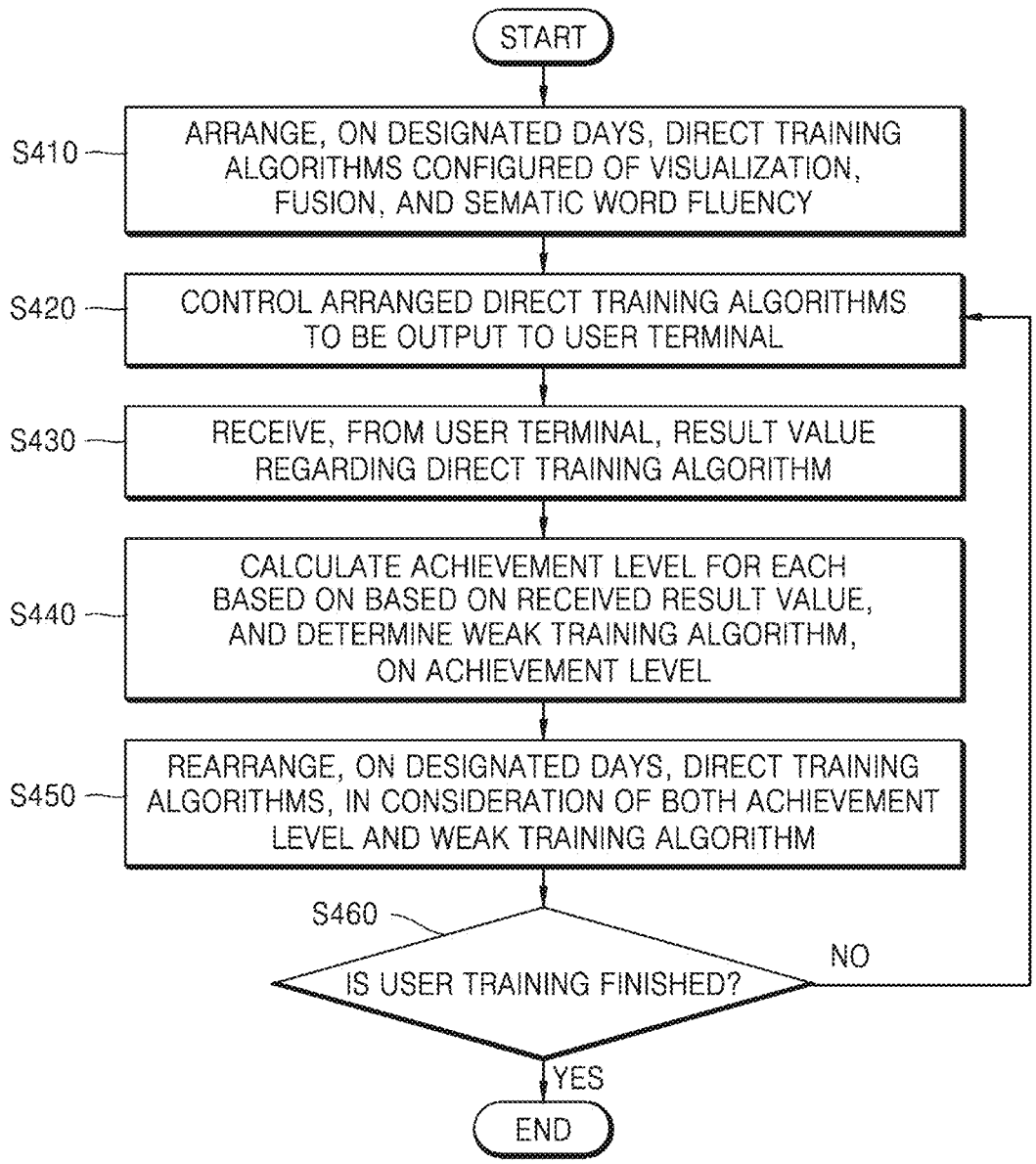

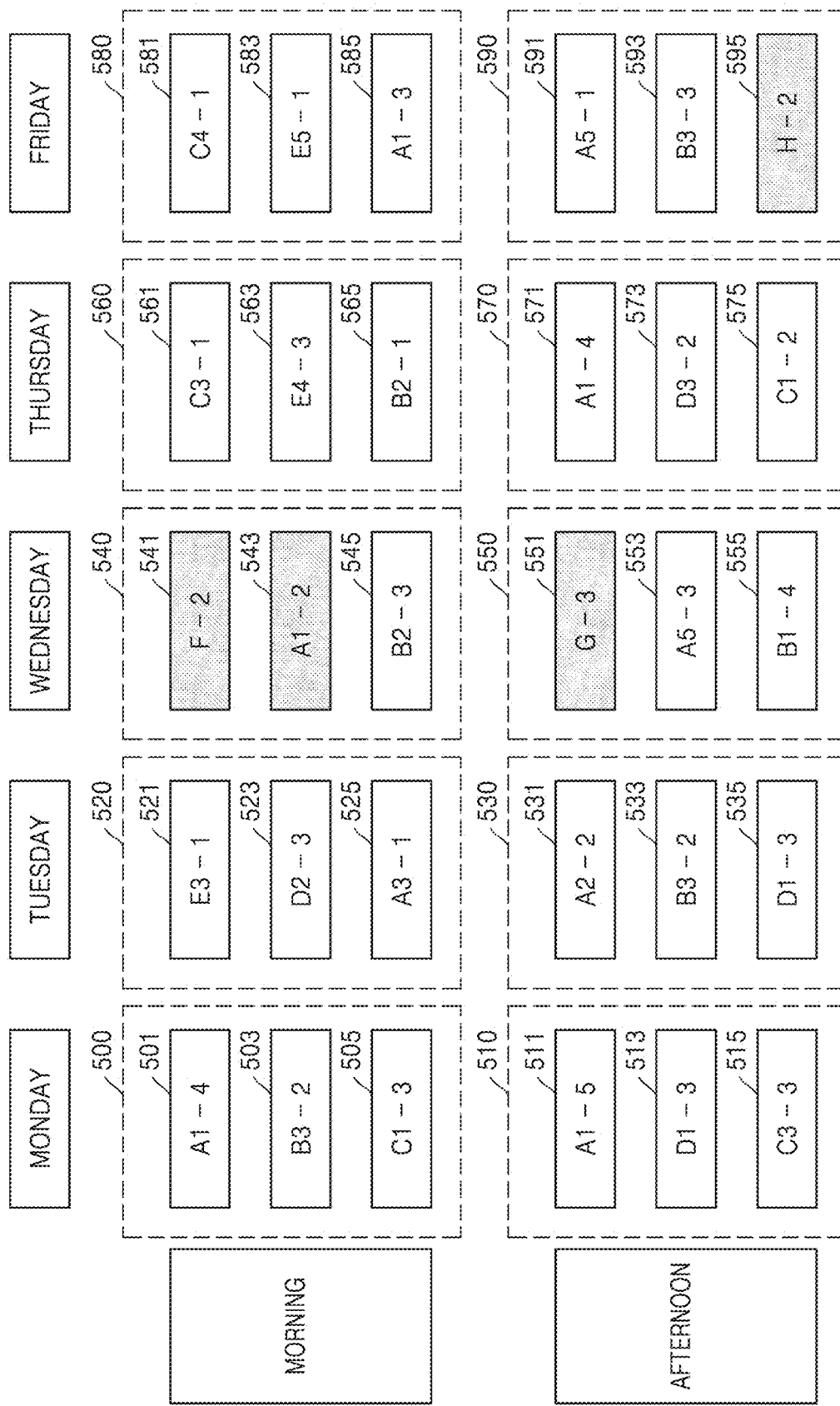

METHOD AND SYSTEM FOR CONSTRUCTING TRAINING PROGRAM FOR IMPROVING SYMPTOMS OF MILD COGNITIVE IMPAIRMENT PATIENT

CROSS-REFERENCE TO RELATED APPLICATION

This application claims the benefit of Korean Patent Application No. 10-2021-0104738, filed on Aug. 9, 2021, and Korean Patent Application No. 10-2021-0153942, filed on Nov. 10, 2021 in the Korean Intellectual Property Office, the disclosure of each of which is incorporated herein in its entirety by reference.

BACKGROUND

1. Field

The disclosure relates to a method of constructing a training program for improving symptoms of a patient, and a system therefor, and more particularly, to a method of composing digital anti-dementia drugs capable of improving symptoms of a mild cognitive impairment patient, and a system for implementing the method.

2. Description of Related Technology

It is evaluated that Republic of Korea has already entered an aging society. As the aging society progresses, the number of dementia patients rapidly increases, and social costs incurred to treat and care for the dementia patients are bound to increase gradually.

SUMMARY

Provided are digital anti-dementia drugs capable of improving symptoms of cognitive impairment patients.

Additional aspects will be set forth in part in the description which follows and, in part, will be apparent from the description, or may be learned by practice of the presented embodiments.

According to an embodiment of the disclosure, a method of constructing a training program for improving symptoms of a mild cognitive impairment patient, includes: arranging, on designated days, direct training algorithms regarding at least one of visualization, fusion, and semantic word fluency directly related to a cognitive function area of a person; controlling the arranged direct training algorithms to be output to a user terminal according to the designated days, and receiving a result value regarding the direct training algorithms from the user terminal; calculating an achievement level for each of the direct training algorithms, based on the result value, and determining one of the direct training algorithms based on the calculated achievement level; and rearranging the direct training algorithms on the designated days, together with the determined direct training algorithm, wherein the rearranging considers both the calculated achievement level and a training algorithm matched to the determined direct training algorithm.

The direct training algorithms may include a training algorithm regarding a working memory and cognitive agility.

The designated days may be determined by information received from the user terminal.

The arranging of the direct training algorithms on the designated days may include arranging different direct training algorithms in morning and afternoon of each day.

The arranging of the direct training algorithms on the designated days may include arranging two or more direct training algorithms in the morning and afternoon of each day.

The method may further include arranging indirect training algorithms regarding word categorization, a changed word search, and past news listening indirectly related to the cognitive function area of the person such as not to overlap the direct training algorithms on the designated days, wherein the receiving of the result value may include controlling the arranged direct training algorithms and indirect training algorithms to be output the user terminal according to the designated days, and receiving result values regarding the direct training algorithms and the indirect training algorithms from the user terminal, and the determining of one of the direct training algorithms may include calculating achievement levels for each of the direct training algorithms and each of the indirect training algorithms, based on the result values, and determining one of the direct training algorithms based on the calculated achievement levels.

The direct training algorithms and the indirect training algorithms may be dividedly arranged in mornings and afternoons of the designated days, and a pre-set indirect training algorithm from among the indirect training algorithms may be fixedly arranged in the afternoons of some days from among the designated days.

According to another embodiment of the disclosure, a system for constructing a training program for improving symptoms of a mild cognitive impairment patient, includes: a first arrangement operation unit for arranging, on designated days, direct training algorithms regarding at least one of visualization, fusion, and semantic word fluency directly related to a cognitive function area of a person; an output control unit for controlling the arranged direct training algorithms to be output to a user terminal according to the designated days; a communication unit for receiving, from the user terminal, a result value regarding the direct training algorithms; a weak training determination unit for calculating an achievement level for each of the direct training algorithms, based on the result value, and determining one of the direct training algorithms based on the calculated achievement level; and a second arrangement operation unit for rearranging the direct training algorithms on the designated days, together with the determined direct training algorithm, wherein the rearranging considers both the calculated achievement level and a training algorithm matched to the determined direct training algorithm.

The direct training algorithms may include a training algorithm regarding a working memory and cognitive agility.

The designated days may be determined by information received from the user terminal.

The first arrangement operation unit may arrange different direct training algorithms in morning and afternoon of each day.

The first arrangement operation unit may arrange two or more direct training algorithms in the morning and afternoon of each day.

The first arrangement operation unit may arrange indirect training algorithms regarding word categorization, a changed word search, and past news listening indirectly related to the cognitive function area of the person such as not to overlap the direct training algorithms on the designated days, the communication unit may control the arranged direct training algorithms and indirect training algorithms to be output the user terminal according to the designated days, and receive result values regarding the direct training algorithms and the indirect training algorithms from the user terminal, and the weak training determination unit may calculate achievement levels for each of the direct training algorithms and each of the indirect training algorithms, based on the result values, and determine one of the direct training algorithms based on the calculated achievement levels.

The first arrangement operation unit may dividedly arrange the direct training algorithms and the indirect training algorithms in mornings and afternoons of the designated days, and fixedly arrange a pre-set indirect training algorithm from among the indirect training algorithms in the afternoons of some days from among the designated days.

According to another embodiment of the disclosure, a computer-readable recording medium has stored therein a program for executing the method.

BRIEF DESCRIPTION OF THE DRAWINGS

These and/or other aspects will become apparent and more readily appreciated from the following description of the embodiments, taken in conjunction with the accompanying drawings.

FIG. 4 is a flowchart of a method according to an embodiment of the disclosure.

FIG. 5 is a diagram schematically showing a training program according to an embodiment of the disclosure.

DETAILED DESCRIPTION

Figure 1:
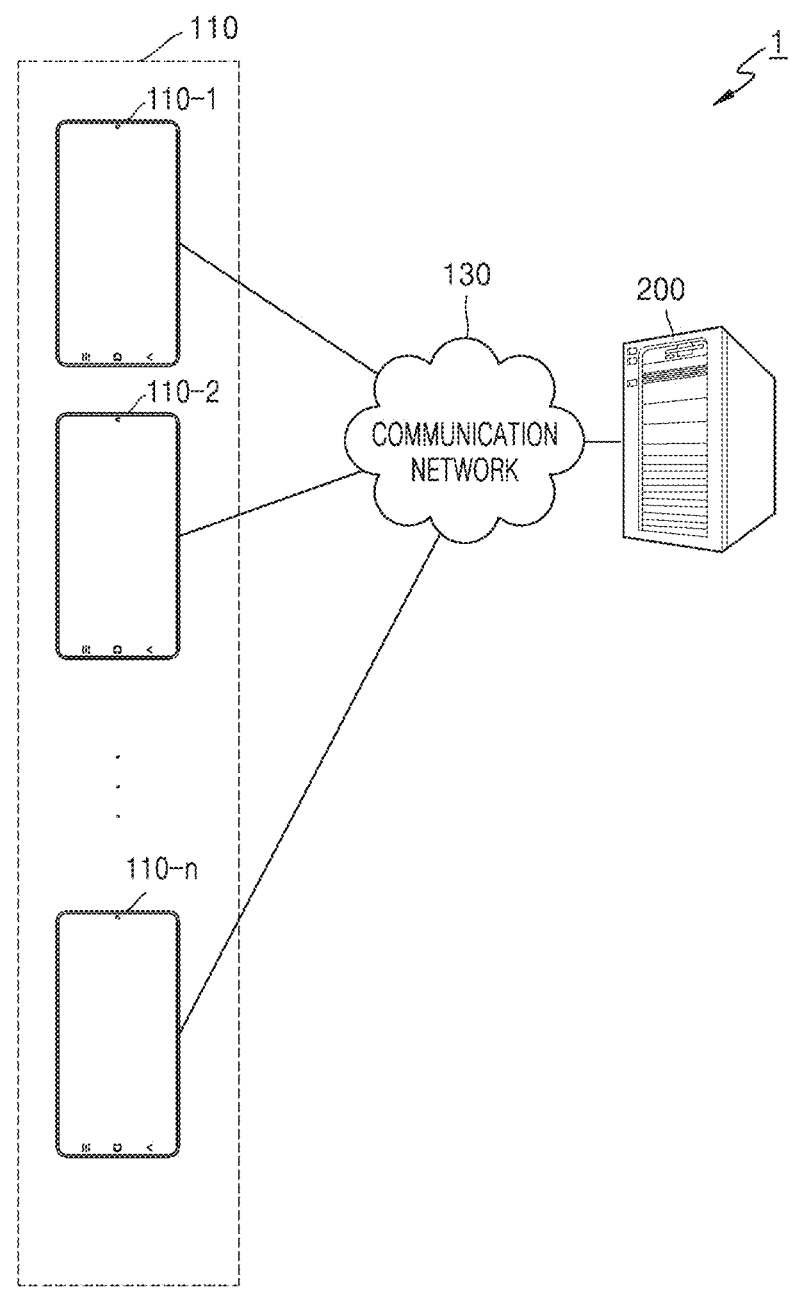
FIG. 1 is a diagram schematically showing an entire system for implementing the disclosure.

It has already been proven that training for stimulating cognitive functions is effective in preventing dementia and improving symptoms of dementia that is already occurred, and that, through several papers, when patients with mild cognitive impairment corresponding to a prior stage of dementia are trained to improve cognitive functions, the cognitive functions significantly improve compared to a patient who already has dementia.

The disclosure may have various modifications and various embodiments, and specific embodiments are illustrated in the drawings and are described in detail in the detailed description. Effects and features of the disclosure and methods of achieving the same will become apparent with reference to embodiments described in detail with reference to the drawings. However, the disclosure is not limited to the embodiments described below, and may be implemented in various forms.

Hereinafter, embodiments of the disclosure will be described in detail with reference to the accompanying drawings, and in the following description with reference to the drawings, like reference numerals refer to like elements and redundant descriptions thereof will be omitted.

In the following embodiments, the terms "first" and "second" are not used in a limited sense and are used to distinguish one component from another component.

In the following embodiments, an expression used in the singular encompasses the expression of the plural, unless it has a clearly different meaning in the context.

In the following embodiments, it will be further understood that the terms "comprise" and/or "comprising" used herein specify the presence of stated features or components, but do not preclude the presence or addition of one or more other features or components.

When a certain embodiment may be implemented differently, a specific process order may be performed differently from the described order. For example, two consecutively described processes may be performed substantially at the same time or performed in an order opposite to the described order.

FIG. 1 is a diagram schematically showing an entire system for implementing the disclosure.

Referring to FIG. 1, a system 1 for constructing a training program, according to the disclosure, has a structure in which a user terminal group 110 and a management server 200 are connected through a communication network 130

The user terminal group 110 may include at least one user terminal. For example, the number of user terminals included in the user terminal group 110 may be one or may be n as shown in FIG. 1. In FIG. 1, n may be an integer equal to or greater than 1.

Each user terminal included in the user terminal group 110 is a terminal of users using a training program according to the disclosure, and denotes an electronic device equipped with a communication module capable of communicating with the management server 200.

The user terminal denotes a smart device including an input device for receiving an input of a user, an output device (display) for visually outputting an input of the user terminal or a processing result of the user terminal, and a communication module capable of communicating with an external device, and thus the size or type of the user terminal is not limited as long as the user terminal includes the input device, the output device, and the communication module. For example, the user terminal is shown in a form of a smart phone in FIG. 1, but the user terminal may be a personal computer (PC), a laptop computer, a netbook, or the like, which is capable of communicating with the management server 200.

The user using the user terminal may denote a person using a training program for improving symptoms of a cognitive impairment patient, and may be a patient who has been diagnosed with cognitive impairment, or a guardian of the patient. As another example, the user may be a tester for improving performance of the training program by repeatedly executing the training program.

The management server 200 is a server on which an integrated management program is installed, and denotes a server that manages and controls a data flow while communicating with a plurality of user terminals included in the user terminal group 110. The integrated management program (integrated management app) is installed in the management server 200, and according to an embodiment, a part of the integrated management program may be implemented in a form of a client driven by the user terminal and installed in the user terminals included in the user terminal group 110.

The communication network 130 performs a function of connecting the user terminal included in the user terminal group 110 with the management server 200, and may include various wired and wireless communication networks, such as a data network, a mobile communication network, and the Internet.

In the disclosure, the training program denotes a logical device capable of controlling a screen output from the user terminal included in the user terminal group 110 under control by the management server 200. The training program does not have a physical form and goes through, several times, processes of being optimized for a user using the training program. In other words, the training program may be continuously updated based on an input input by the user through the user terminal and a command received from the management server 200. Mild cognitive impairment symptoms may improve when mild cognitive impairment patents repeatedly use the training program driven by the user terminal.

In the disclosure, the training program may include at least one direct training algorithm. Also, as another example, the training program may include at least one direct training algorithm and at least one indirect training algorithm. Hereinafter, unless specifically limited, the training algorithm is considered to include a direct training algorithm and an indirect training algorithm.

The training program may be implemented in a form in which the direct training algorithm or the indirect training algorithm is output according to a pre-set order, through the user terminal. The order in which the training algorithm is output through the user terminal may be different for each user. For example, when a user A drives the training program, contents output from the user terminal may be changed in an order of a direct training algorithm-1, a direct training algorithm-2, and a direct training algorithm-3, and when a user B drives the training program, the direct training algorithm-2, an indirect training algorithm-3, and the direct training algorithm-1 may be sequentially output to a user terminal of the user B.

The user may apply an input to the direct training algorithm or the indirect training algorithm that is in a test form and output to the user terminal, and values calculated according to the input of the user may be used to update the training program corresponding to the user.

Figure 2:
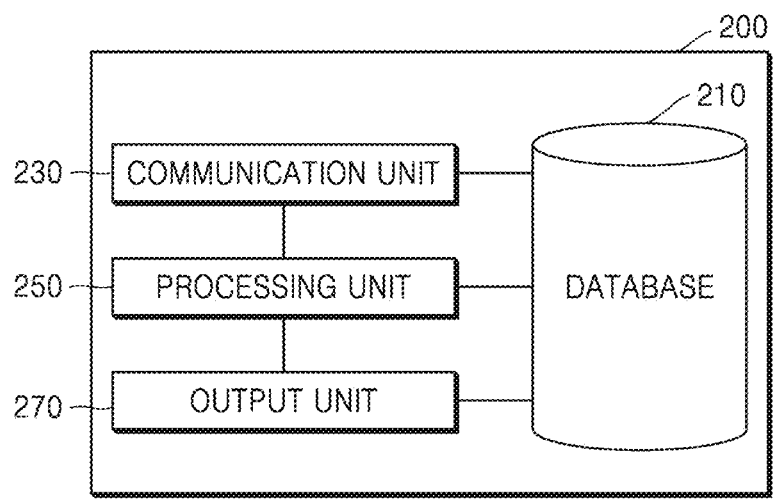
FIG. 2 is a block diagram of a management server for implementing a method of constructing a training program, according to an embodiment of the disclosure.

FIG. 2 is a block diagram of the management server 200 for implementing a method of constructing a training program, according to an embodiment of the disclosure.

Referring to FIG. 2, the management server 200 according to an embodiment of the disclosure includes a database 210, a communication unit (a communication circuit, a communication processor, or a communication interface) 230, a processing unit 250, and an output unit 270.

The management server 200 according to an embodiment of the disclosure may correspond to at least one processor, or may include at least one processor. Accordingly, the management server 200 and the communication unit 230, the processing unit 250, and the output unit 270 included in the management server 200 may be driven by being included in a hardware device, such as a microprocessor or a general-purpose computer system.

A name of each module included in the management server 200 shown in FIG. 2 is arbitrarily named to intuitively describe a representative function performed by each module, and when the management server 200 is actually implemented, each module may be given a name different from the name shown in FIG. 2.

In addition, the number of modules included in the management server 200 of FIG. 2 may vary each time according to an embodiment. In particular, the management server 200 of FIG. 2 includes a total of three modules, but according to an embodiment, at least two modules may be integrated into one module, or at least one module may be separated into two or more modules.

The database 210 stores various types of data necessary for the management server 200 to operate. For example, the database 210 stores the integrated management program for controlling operations of the management server 200, and may receive data received by the communication unit 230 from the user terminal and store the same.

The communication unit 230 communicates with the user terminal included in the user terminal group 110.

The processing unit 250 processes data received by the communication unit 230 and data to be transmitted. Data processed by the processing unit 250 includes data received from the user terminal or to be transmitted to the user terminal.

As an embodiment, the processing unit 250 may combine the data received by the communication unit 230 with information stored in the database 210 and process the same, or may perform a function of issuing a command for the communication unit 230 and the output unit 270 to suitably operate to implement a method according to the disclosure.

A function performed by the processing unit 250 is not limited to a specific function, and although the processing unit 250 is illustrated as a single module in FIG. 2, the processing unit 250 may be subdivided into a plurality of modules according to processes of the processing unit 250. The processing unit 250 including subdivided modules will be described below with reference to FIG. 3.

The output unit 270 receives commands from the processing unit 250 to calculate and output various types of data.

Figure 3:
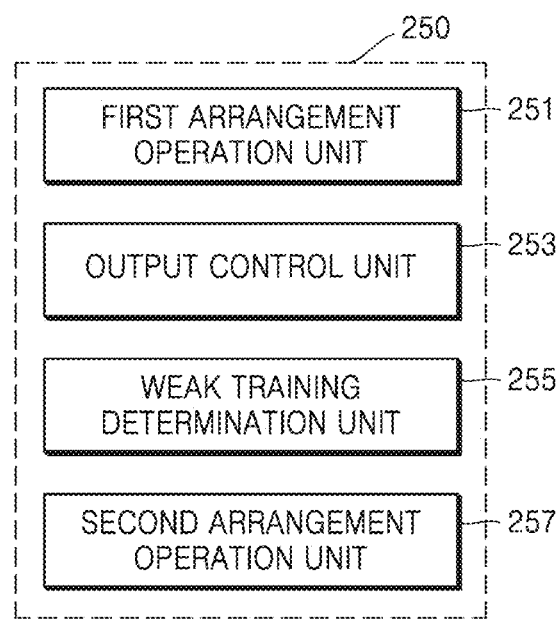
FIG. 3 is a block diagram showing an example of a processing unit subdivided according to functions.

FIG. 3 is a block diagram showing an example of the processing unit 250 subdivided according to functions.

Referring to FIG. 3, the processing unit 250 includes a first arrangement operation unit (or a first arrangement operation processor) 251, an output control unit (or an output control processor) 253, a weak training determination unit (or a weak training determination processor) 255, and a second arrangement operation unit (or a second arrangement operation processor) 257.

The first arrangement operation unit 251, the output control unit 253, the weak training determination unit 255, and the second arrangement operation unit 257 included in the processing unit 250, according to an embodiment of the disclosure, may be driven by being included in a hardware device, such as a microprocessor or a general-purpose computer system. A name of each module included in the processing unit 250 shown in FIG. 3 is arbitrarily named to intuitively describe a representative function performed by each module, and when the processing unit 250 is actually implemented, each module may be given a name different from the name shown in FIG. 3.

The first arrangement operation unit 251 performs a function of arranging, on designated days, a direct training algorithm regarding at least one of visualization, fusion, semantic word fluency, working memory, and cognitive agility directly related to a cognitive function area of a person. Here, the visualization, the fusion, the semantic word fluency, the working memory, and the cognitive agility are training algorithms structured in different manners, and for example, the direct training algorithm regarding the visualization denotes an algorithm for letting a user to hear voice describing a specific situation and picture a scene in his/her head, thereby directly stimulating a cognitive function of the user.

TABLE 1

| Direct Training Algorithm | Detailed Training Algorithm |
| --- | --- |
| Visualization | Visualization Training |
| Semantic Word Fluency | Semantics Training |
| Fusion | Fusion Training A |
|  | Fusion Training B |
| Working Memory | Span Expansion Training |
|  | Work Training |
| Cognitive Agility | Processing Speed Training |

Table 1 shows the direct training algorithms and detailed training algorithms for improving symptoms of cognitive impairment. Five types of algorithms in Table 1 may help cognitive impairment patients to recover their symptoms in different directions.

Hereinafter, Tables 2 to 8 show examples of direct training algorithms implemented through a user terminal.

TABLE 2

Did you hear it well?
What comes to mind?
Do you remember any lines of characters?
Did the scenes of the movie picture well in mind?

Table 2 shows an example of visualization training. The visualization training as shown in Table 2 uses a recollection therapy of bringing back a patient's memory of youth through a voice drama to stimulate cognitive skill of the patient and help the patient to restore identity and self-esteem.

TABLE 3

We will play a game called Find Word now.
Please tell me what comes to mind after hearing a word.
Let's start.
The first word is an apple.
What comes to mind when you think of an apple?
What comes to mind? (7 seconds)
Sweetness comes to mind.
Any other word that comes to mind? (5 seconds)
Good job.

Table 3 shows an example of semantics training. The semantics training as shown in Table 3 allows a user to freely speak an associated word, thereby activating a network between long-term memories of the user.

TABLE 4

We will play Make Story this time.
You can remember a word better when you make a story.
Let me make a story first using an apple and a camel we remembered just before.
How about an apple that slipped from a camel's hump?
Now you make a story using an apple and a camel. (8 seconds)
Good job.

Table 4 shows an example of a training algorithm corresponding to fusion training A. The fusion training A helps a user to efficiently use his/her memory through an experience of continuous elaboration process.

TABLE 5

Today, let's say some words from your imagination.
Please tell me everything you remember. (10 seconds)
I see.
I will check if you remember them until tomorrow.
Please keep them in mind.

Table 5 shows an example of a training algorithm corresponding to fusion training B. The fusion training B may help a user to experience an elaboration process through visual imaging.

TABLE 6

Let's play a game called Add On Fruits today.
Apple,
Apple-Strawberry,
Apple-Strawberry-Grapes,
Apple-Strawberry-Grapes-Peaches
I can't remember anymore.
You won. Your memory is really incredible.

Table 6 shows an example of a training algorithm corresponding to span expansion training. Through the training as shown in Table 6, a user may experience an interaction of alternately speaking, and rebuild or stimulate a neural network of a brain.

TABLE 7

We will play a reverse game today.
For example, when 1 say "eat watermelon", you say "watermelon eat".
. . .
Good job.

Table 7 shows an example of a training algorithm corresponding to work training. Through the training as shown in Table 7, a user may improve auditory short-term memory.

TABLE 8

Today, we will do healthy claps.
Whenever you see the word clap, please clap. (60 seconds)
Good job.

Table 8 shows an example of a training algorithm corresponding to processing speed training. A user may improve a cognitive control function, attention, and a processing speed through the training as shown in Table 8.

Although there are various methods to directly stimulate a cognitive function of a person, algorithms determined to be most effective in improving symptoms of a mild cognitive impairment patients in the disclosure are five types described above (visualization, fusion, semantic word fluency, working memory, and cognitive agility).

The first arrangement operation unit 251 arranges the above-described five types of algorithms on designated days. Here, the designated days denote days designated by a user or the processing unit 250 from among the Monday, Tuesday, Wednesday, Thursday, Friday, Saturday, and Sunday constituting a week, and generally, the designated days are days on which the user is able to participate in a training program. For example, the designated days may be Monday, Tuesday, Wednesday, Thursday, and Friday, which are weekdays, and the user may add or exclude specific days through an input.

The first arrangement operation unit 251 may arrange at least one of the five types of training algorithms on the designated days. For example, a direct training algorithm-1 may be arranged on Monday, and a direct training algorithm-2 may be arranged on Tuesday. Initial arrangement of the training algorithms performed by the first arrangement operation unit 251 may be default arrangement pre-set in the first arrangement operation unit 251 or randomly selected arrangement. While the training programs are repeatedly driven, the training programs are updated according to characteristics of the user, and thus the initial arrangement of the training algorithm is not particularly limited.

The output control unit 253 may control the direct training algorithms arranged by the first arrangement operation unit 251 to be output from the user terminal according to designated days. In detail, the output control unit 253 transmits the direct training algorithms of which the arrangement is confirmed to the communication unit 230 so that the communication unit 230 transmits the same to the user terminal.

The user performs training for improving cognitive impairment symptoms, based on the direct training algorithms output through the user terminal, and a result value of the training calculated by the user terminal is received by the communication unit 230.

The weak training determination unit 255 may calculate an achievement level for each direct training algorithm based on the received result value of the training, and determine one of the direct training algorithms based on the calculated achievement level. For example, the weak training determination unit 255 may determine a direct training algorithm corresponding to a lowest achievement level such that the direct training algorithm is executed in a training program executed next. The direct training algorithm determined by the weak training determination unit 255 is a training algorithm for updating a training program in which the user participated immediately before, and may replace one of a plurality of training algorithms included in the training program.

The second arrangement operation unit 257 rearranges the direct training algorithms on the designated days together with the direct training algorithm determined by the weak training determination unit 255. The second arrangement operation unit 257 rearranges the direct training algorithms on the designated days, in consideration of both the achievement level calculated immediately before and a training algorithm matching the determined direct training algorithm.

training program is arranged one more time, and an order of the training algorithms is different from the initial arrangement for each day.

Each direct training algorithm includes a matching training algorithm as metadata. The matching training algorithm denotes an algorithm that has been verified experimentally, empirically, and mathematically to enhance a training effect by being arranged prior to the direct training algorithm. For example, when a result value of Training-2 is higher when the user performs Training-2 after performing Training-1 than when the user only performs Training-2, Training-1 may be a matching training algorithm of Training-2. A training algorithm matching a direct training algorithm will be described in detail with reference to FIG. 5.

FIG. 4 is a flowchart of a method according to an embodiment of the disclosure.

The method according to FIG. 4 may be implemented by the management server 200 or the processing unit 250 described with reference to FIGS. 2 and 3, and hereinafter, will be described below with reference to FIG. 3.

The first arrangement operation unit 251 arranges, on the designated days, the direct training algorithms configured of visualization, fusion, and semantic word fluency (operation S410).

The output control unit 253 controls the arranged direct training algorithms to be output to the user terminal (operation S420).

The communication unit 230 receives, from the user terminal, the result value regarding the direct training algorithm (operation S430).

The weak training determination unit 255 calculates an achievement level for each algorithm, based on the received result value, and determines a weak training algorithm, based on the achievement level (operation S440).

The second arrangement operation unit 257 rearranges, on the designated days, the direct training algorithms, in consideration of both the achievement level and the weak training algorithm (operation S450).

The processing unit 250 may determine whether training of the user is finished (operation S460), and when the training is not finished, control the rearranged direct training algorithms to be output to the user terminal (operation S420). In this case, operation S420 is second training for the user.

FIG. 5 is a diagram schematically showing a training program according to another embodiment of the disclosure.

In FIG. 5, a record of a user participating in a training program is updated on a weekly basis. For example, a case

TABLE 9

|  | Monday | Tuesday | Wednesday | Thursday | Friday |
|---|---|---|---|---|---|
| Initial Arrangement | Training-1 | Training-2 | Training-3 | Training-4 | Training-5 |
| Rearrangement | Training-1 | Training-2 | Training-4 | Training-1 | Training 3 |

Table 9 shows an example of the rearranged direct training algorithms.

Referring to Table 9, regarding training algorithms constituting the training program, Training-1 to Training-5 are sequentially arranged from Monday to Friday in initial arrangement, but when the training algorithms are rearranged, Training-5 is excluded, Training-1 that showed a lowest achievement level when the user first participated the in which the user performed the training program from Monday to Friday may be distinguished as first training, and a case in which the user performed the training program from following Monday to Friday may be distinguished as second training.

As shown in FIG. 5, it is assumed that one training program is conducted only from Monday to Friday. The training program according to FIG. 5 includes a total of 30 training algorithms, and the training algorithms included in the training program may include a direct training algorithm and an indirect training algorithm. For convenience of description, only the total of 30 training algorithms are shown in FIG. 5, but the number of training algorithms arranged to construct the training program may vary according to embodiments. For example, as shown in Table 9, the training program may be constructed with five training algorithms.

After days are designated, the processing unit 250 may generate a template such that the training algorithms for constructing the training program are arranged according to the designated days. In FIG. 5, morning and afternoon are divided for each day, and virtual slots are provided such that three training algorithms are arranged each in the morning and afternoon of each day. According to an embodiment, each of the numbers of slots of the morning and afternoon may not be three, and the numbers of slots in the morning and afternoon may be different from each other.

The indirect training algorithm is a concept distinguished from the already-described direct training algorithm, and refers to a training algorithm indirectly related to a cognitive function area of a person. The indirect training algorithm may include word categorization, a changed word search, and past news listening.

The word categorization denotes a training algorithm that shows a plurality of words to a user and enables the user to classify the plurality of words into several groups, based on commonalities of the words. The changed word search denotes a training algorithm that shows some sentences to the user and allows the user to find a changed word. The past news listening denotes a training program that stimulates the user's cognitive function by composing events that occurred in the user's 20s and 30s like news.

The indirect training algorithm does not largely stimulate the user's cognitive function compared to the above-described five types of direct training algorithms, but when the training program is constructed with the direct training algorithms, the indirect training algorithm may be effective in improving cognitive impairment symptoms of the user.

In addition, the indirect training algorithm may also be a training algorithm recorded in metadata of the direct training algorithm. For example, metadata of fusion training A (story making training) described in Table 4 may include the word categorization, and when the user first performs the word categorization first and then makes a story as shown in Table 4, an achievement level of story making may be further improved.

As described above, the direct training algorithm includes at least one training algorithm as metadata, and when the user's achievement level regarding a specific direct training algorithm is low, the user is trained by a training algorithm included in the metadata immediately before being trained by the direct training algorithm that has a low achievement level so as to improve the achievement level, thereby effectively stimulating the user's cognitive function and inducing recovery of the cognitive function. In the disclosure, the metadata set for each training algorithm is determined by empirical, mathematical, experimental, and statistical data.

Hereinafter, for convenience of description, training that is performed first will be referred to as a first trial, and training that is performed next will be referred to as a second trial. In addition, in FIG. 5, a slot in which a training algorithm performed first on Monday morning is arranged will be referred to as a first slot 501, a slot in which a training algorithm performed latest on Friday afternoon is arranged will be referred to as a 30th slot 595, and slots between the first slot 501 and the 30th slot 595 will be referred to according to a similar rule.

The first arrangement operation unit 251 may arrange the training algorithms in the morning and afternoon of Monday to Friday. Because there is no data about the user in the first trial, the first arrangement operation unit 251 may arrange the training algorithm in empty slots of the training program according to default arrangement, or may randomly arrange the training algorithms when there is no default arrangement.

In FIG. 5, among the training algorithms arranged in the slots, a training algorithm starting with A, B, C, D, or E denotes a direct training algorithm, and a training algorithm starting with F, G, or H denotes an indirect training algorithm. Hereinafter, A to H may be referred to as training codes.

A number written immediately after the training code in FIG. 5 denotes a detailed training algorithm described in Table 1. For example, when there are four detailed training algorithms in a direct training algorithm regarding visualization, the four detailed training algorithm may be referred to as A1, A2, A3, and A4, respectively. Hereinafter, a number written after the training code may be referred to as a training number.

A number written after the training number in FIG. 5 denotes a level of corresponding training. Even when training algorithms have a same training number, the higher the level, the higher the stimulation for the user's cognitive function.

In summary, a second slot 503 of FIG. 5 is a training algorithm having a training number 3 from among training algorithms regarding semantic word fluency (B), and a training level thereof is 2. As another example, a fourth slot 511 of FIG. 5 is a training algorithm having a training number 1 from among training algorithms for visualization (A), and a training level thereof is 5.

After the training algorithm is arranged in each slot included in the training program by the first arrangement operation unit 251, construction of the training program is completed. The constructed training program is transmitted to a user terminal such that the user may drive the training program and participate in the training program through the user terminal. The communication unit 230 may receive a result value regarding each training algorithm constituting the training program from the user terminal and transmit the same to the weak training determination unit 255.

The weak training determination unit 255 calculates an achievement level for each training algorithm based on the result value, and determines one training algorithms based on the calculated achievement level. During this process, the weak training determination unit 255 determines a training algorithm having a lowest achievement level as a weak training algorithm of the user, and controls training for a corresponding area to be intensively continued.

The second arrangement operation unit 257 reconstructs the training program for the second trial together with the direct training algorithm determined by the weak training determination unit 255. The reconstructed training program may be reconstructed such that the weak training algorithm determined by the weak training determination unit 255 is included again, and additionally in consideration of the achievement level of each training algorithm calculated by the weak training determination unit 255.

The training program shown in FIG. 5 is an example of a training program reconstructed through the above processes. First, a training algorithm determined as the weak training algorithm in the first trial is an A1-2 training algorithm of a 14th slot 543 included in Wednesday morning training 540. The weak training determination unit 255 determines that the user's achievement level regarding the A1-2 training algorithm is low when a correct answer rate is 0 and a training level is 2 or higher regarding the A1-2 training algorithm, and searches for preceding training by referring to metadata of the A1-2 training algorithm.

As the user repeatedly uses the training program, the achievement level is continuously updated, and the arrangement of the training algorithms constituting the training program as a whole is also changed.

According to FIG. 5, the preceding training of the A1-2 training algorithm is an F-2 training algorithm, and the F-2 algorithm may be arranged immediately before the A1-2 training algorithm to induce improvement in the user's achievement level of the A1-2 training algorithm. As already described, the preceding training included in the metadata may be a direct training algorithm or an indirect training algorithm.

In particular, in the disclosure, in order to effectively stimulate the user's cognitive function, the first arrangement operation unit 251 and the second arrangement operation unit 257 may configure the training program such that a day divided into morning and afternoon for training, and fixedly arrange a pre-set indirect training algorithm in afternoon of some days. Referring to FIG. 5, a G-3 training algorithm corresponding to a changed word search level 3 may be arranged in a 16th slot 551 of Wednesday afternoon training 550, and an H-2 training algorithm corresponding to a past news listening level 2 may be fixedly arranged in the 30th slot 595 of Friday afternoon training 590, thereby effectively stimulating the user's cognitive function and inducing symptom relief.

The second arrangement operation unit 257 may simultaneously consider the user's achievement level and training level when rearranging training algorithms of remaining slots, except for the weak training algorithm or the fixedly-arranged indirect training algorithm.

For example, when levels of detailed training achieved by the user in training belonging to a working memory area (D) during the first trial are 3 for word stacking, 4 for word order, and 5 for reverse speaking, a level of the user regarding the working memory area (D) is set to 4, and such a level value is considered when the training algorithms are rearranged. At this time, an achievement level regarding the working memory area is 4.

As another example, when achievement levels of training of the user during the first trial are 1 for visualization training, 1 for fusion training, 4 for working memory training, 2 for semantic word fluency training, and 2 for cognitive agility training, training algorithms arranged in the training program during the second trial may be determined as a reciprocal of the achievement level of each training is applied as a weight. According to the above numerical values, the weights for training are 30%, 30%, 8%, 16%, and 16%, respectively, and thus in the second trial, the visualization training and the fusion training may be included with a largest proportion and the working memory training may be included with a smallest proportion for the training algorithms arranged in the training program. Such weight calculation may also be applied when a detailed training algorithm of same training is determined.

According to the disclosure, symptoms of mild cognitive impairment patients may be greatly improved.

According to the disclosure, dementia that is most feared disease of the elderly may be prevented or diagnosed at an early stage.

According to the disclosure, it is possible to significantly reduce social costs of managing dementia patients.

According to the disclosure, unlike existing technologies, it is possible to stimulate memory formation processes of cognitive impairment patients in memory units through visualization, semantic word fluency, and fusion training, and comprehensively improve working memory abilities and processing speeds.

A training program constructed according to the disclosure may effectively stimulate a brain region responsible for a user's cognitive function, thereby improving a thickness of cerebrocortex and the cognitive function, and regarding the brain of the user who has experienced the training program according to the disclosure, an increase in brain volume including changes in the whole white matter has been confirmed through DT1 imaging.

According to the disclosure, symptoms of mild cognitive impairment patients can be greatly improved.

According to the disclosure, dementia that is most feared disease of the elderly can be prevented or diagnosed at an early stage.

According to the disclosure, it is possible to significantly reduce social costs of managing dementia patients.

According to the disclosure, unlike existing technologies, it is possible to stimulate memory formation processes of cognitive impairment patients in memory units through visualization, semantic word fluency, and fusion training, and comprehensively improve working memory abilities and processing speeds.

The embodiments according to the disclosure described above may be implemented in a form of a computer program executable by various components on a computer, and such a computer program may be recorded in a computer-readable medium. Here, the computer-readable recording medium may include hardware devices specially designed to store and execute program instructions, such as magnetic media, such as a hard disk, a floppy disk, and a magnetic tape, optical recording media, such as CD-ROM and DVD, magneto-optical media such as a floptical disk, and read-only memory (ROM), random-access memory (RAM), and a flash memory.

The program commands may be specially designed for the disclosure or well known to one of ordinary skill in the computer software field. Examples of the computer program include not only machine codes generated by a compiler, but also high-level language codes executable by a computer by using an interpreter or the like.

Certain executions described in the disclosure are embodiments and do not limit the scope of the disclosure in any way. For brevity of the specification, general electronic configurations, control systems, software, and other functional aspects of systems may be omitted. In addition, connection or connection members of lines between components shown in the drawings exemplarily represent functional connections and/or physical or circuit connections, and in an actual apparatus, may be replaced or may be implemented as various additional functional connections, physical connections, or circuit connections. Also, elements described herein may not be essential elements for application of the disclosure unless the elements are particularly described as being "essential" or "critical".

The term "the" and similar referential terms in the specification (specifically in the claims) of the disclosure may be used for both the singular and the plural. Further, when a range is described in the disclosure, the disclosure includes inventions to which individual values belonging to the range are applied (unless otherwise stated), and it is considered that each individual value configuring the range is described in the detailed description of the disclosure. Lastly, unless an order is clearly stated or unless otherwise stated, operations configuring a method according to the disclosure may be performed in an appropriate order. The disclosure is not necessarily limited by an order the operations are described. In the disclosure, the use of all examples or exemplary terms (for example, "etc.") is merely for describing the disclosure in detail and the scope of the disclosure is not limited by those examples or exemplary terms unless defined in the claims. Also, it would be obvious to one of ordinary skill in the art that various modifications, combinations, and changes may be configured according to design conditions and factors within the scope of claims or equivalents.

What is claimed is:

1. A method of constructing a training program for improving symptoms of a mild cognitive impairment patient, the method comprising:
   providing a server computer configured to be connected to and communicate with a user terminal group through a communication network, the user terminal group comprising one or more user terminals, the server computer comprising a microprocessor configured to implement a first arrangement operation processor, an output control processor, a weak training determination processor, a second arrangement processor, and a communication interface, the server computer further comprising a database configured to store an integrated management program for controlling operations of the server computer, and data received from the user terminal group;
   establishing, by the communication interface, a communication link with a selected user terminal of the one or more user terminals, the selected user terminal associated with a user and configured to store a training program, the training program comprising one or more direct training algorithms and one or more indirect training algorithms; and
   controlling, by the microprocessor, a screen output from the selected user terminal to continuously update the training program stored in the selected user terminal based on a user input received by the selected user terminal and a command received from the server computer,
   the controlling comprising:
   arranging, by the first arrangement operation processor, on designated days, the direct training algorithms regarding at least one of visualization, fusion, or semantic word fluency directly related to a cognitive function area of a person;
   arranging, by the first arrangement operation processor, on the designated days, at least one of the indirect training algorithms regarding word categorization, a changed word search, or past news listening indirectly related to the cognitive function area of the person;
   controlling, by the output control processor, the arranged direct training algorithms to be output to the selected user terminal according to an order arranged by the first arrangement operation on the designated days such that the user performs training for improving cognitive impairment symptoms based on the direct training algorithms and the indirect training algorithms arranged by the first arrangement operation processor and output through the selected user terminal,
   receiving, by the communication interface, a result value regarding the direct training algorithms from the selected user terminal;
   calculating, by the weak training determination processor, an achievement level for each of the direct training algorithms, based on the result value, and determining one of the direct training algorithms based on the calculated achievement level, wherein the determined direct training algorithm corresponds to a lowest achievement level among the direct training algorithms; and
   rearranging, by the second arrangement operation processor, the direct training algorithms on the designated days, together with the determined direct training algorithm, to replace one of the direct training algorithms in the order arranged by the first arrangement operation processor with the determined direct training algorithm such that the order arranged by the first arrangement operation processor is updated and optimized for the user,
   Wherein the determined direct training algorithm comprises a metadata indicative of a matched training algorithm which is a selected training algorithm of the training algorithms, wherein a training result value of the determined direct training algorithm is higher when the determined direct training algorithm is performed in the selected user terminal after the matched training algorithm being performed than when the determined direct training algorithm is performed in the selected user terminal without the matched training algorithm being performed, and
   wherein the rearranging comprises arranging the matched training algorithm before the determined direct training algorithm without intervening of any other training algorithm among the direct training algorithms or the indirect training algorithms.

2. The method of claim 1, wherein the direct training algorithms comprise a training algorithm regarding a working memory and cognitive agility.

3. The method of claim 1, wherein the designated days are determined by information received from the selected user terminal.

4. The method of claim 1, wherein the arranging of the direct training algorithms on the designated days comprises arranging different direct training algorithms in morning and afternoon of each day.

5. The method of claim 4, wherein the arranging of the direct training algorithms on the designated days comprises arranging two or more direct training algorithms in the morning and afternoon of each day.

6. The method of claim 1, wherein the direct training algorithms and the indirect training algorithms are dividedly arranged in mornings and afternoons of the designated days, and
   a pre-set indirect training algorithm from among the indirect training algorithms is fixedly arranged in the afternoons of some days from among the designated days.

7. A non-transitory computer-readable recording medium storing instructions to perform the method of claim 1.

8. The method of claim 1, wherein the matched training algorithm is one of the indirect training algorithms.

9. The method of claim 1, wherein the training program comprises the order of the direct training algorithms for the user and a secondary order of the direct training algorithms for a secondary user which is different from the order for the user, and wherein the method comprises outputting the direct training algorithms according to the secondary order to another user terminal for the secondary user.

10. The method of claim 1, wherein the first arrangement operation processor is further configured to arrange the training algorithms according to a default arrangement pre-set or randomly arranges the training algorithms to generate the order.

11. A system for constructing a training program for improving symptoms of a mild cognitive impairment patient, the system comprising:
a communication interface configured to establish a communication link with a selected user terminal of one or more user terminals, the selected user terminal associated with a user and configured to store a training program, the training program comprising one or more direct training algorithms and one or more indirect training algorithms; and
a microprocessor configured to control the communication interface and implement a first arrangement operation processor, an output control processor, a weak training determination processor, a second arrangement processor, and a communication interface, the server computer further comprising a database configured to store an integrated management program for controlling operations of the server computer, and data received from the user terminal group;
the microprocessor further configured to control a screen output from the selected user terminal to continuously update the training program stored in the selected user terminal based on a user input received by the selected user terminal,
the first arrangement operation processor configured to arrange, on designated days, the direct training algorithms regarding at least one of visualization, fusion, or semantic word fluency directly related to a cognitive function area of a person, and arrange, on the designated days, at least one of the indirect training algorithms regarding word categorization, a changed word search, or past news listening indirectly related to the cognitive function area of the person;
the output control processor configured to control the arranged direct training algorithms to be output to the selected user terminal according to an order arranged by the first arrangement operation processor on the designated days such that the user performs training for improving cognitive impairment symptoms based on the direct training algorithms and the indirect training algorithms arranged by the first arrangement operation processor and output through the selected user terminal;
the communication interface configured to receive, from the selected user terminal, a result value regarding the direct training algorithms;
the weak training determination processor configured to calculate an achievement level for each of the direct training algorithms, based on the result value, and determine one of the direct training algorithms based on the calculated achievement level, wherein the determined direct training algorithm corresponds to a lowest achievement level among the direct training algorithms; and
the second arrangement operation processor configured to rearrange the direct training algorithms on the designated days, together with the determined direct training algorithm based on both the calculated achievement level and a training algorithm matched to the determined direct training algorithm to replace one of the direct training algorithms in the order arranged by the first arrangement operation processor with the determined direct training algorithm such that the order arranged by the first arrangement operation processor is updated and optimized for the user,
wherein the determined direct training algorithm comprises a metadata indicative of a matched training algorithm which is a selected training algorithm of the training algorithms, wherein a training result value of the determined direct training algorithm is higher when the determined direct training algorithm is performed in the selected user terminal after the matched training algorithm being performed than when the determined direct training algorithm is performed in the selected user terminal without the matched training algorithm being performed, and
wherein the second arrangement operation processor is further configured to arrange the matched training algorithm before the determined direct training algorithm without intervening of any other training algorithm among the direct training algorithms or the indirect training algorithms.

12. The system of claim 11, wherein the direct training algorithms comprise a training algorithm regarding a working memory and cognitive agility.

13. The system of claim 11, wherein the designated days are configured to be determined by information received from the user terminal.

14. The system of claim 11, wherein the first arrangement operation processor is configured to arrange different direct training algorithms in morning and afternoon of each day.

15. The system of claim 14, wherein the first arrangement operation processor is configured to arrange two or more direct training algorithms in the morning and afternoon of each day.

16. The system of claim 11, wherein the first arrangement operation processor is configured to dividedly arrange the direct training algorithms and the indirect training algorithms in mornings and afternoons of the designated days, and fixedly arrange a pre-set indirect training algorithm from among the indirect training algorithms in the afternoons of some days from among the designated days.

* * * * *